United States Patent
Obel et al.

(10) Patent No.: US 6,748,273 B1
(45) Date of Patent: Jun. 8, 2004

(54) METHOD AND CIRCUIT FOR DETERMINING THE BATTERY STATUS IN A MEDICAL IMPLANT

(75) Inventors: Martin Obel, Danderyd (SE); Niklas Sköldengen, Täby (SE); Jan Lindberg, Sollentuna (SE)

(73) Assignee: St. Jude Medical AB, Järfälla (SE)

( * ) Notice: Subject to any disclaimer, the term of this patent is extended or adjusted under 35 U.S.C. 154(b) by 0 days.

(21) Appl. No.: 10/031,548

(22) PCT Filed: Jun. 16, 2000

(86) PCT No.: PCT/SE00/01295

§ 371 (c)(1),
(2), (4) Date: Jun. 3, 2002

(87) PCT Pub. No.: WO01/05466

PCT Pub. Date: Jan. 25, 2001

(30) Foreign Application Priority Data

Jul. 19, 1999 (SE) ................................ 9902734

(51) Int. Cl.[7] ................................ A61N 1/37
(52) U.S. Cl. ................................ 607/29
(58) Field of Search ................ 607/27, 28, 29

(56) References Cited

U.S. PATENT DOCUMENTS

| | | |
|---|---|---|
| 4,715,381 A | 12/1987 | Moberg |
| 5,370,668 A | 12/1994 | Shelton et al. |
| 5,769,873 A | 6/1998 | Zadeh |
| 2003/0149455 A1 * | 8/2003 | Obel et al. |

FOREIGN PATENT DOCUMENTS

| | | |
|---|---|---|
| EP | 0 739 645 | 10/1996 |
| WO | WO 99/14612 | 3/1999 |

* cited by examiner

*Primary Examiner*—Scott M. Getzow
(74) *Attorney, Agent, or Firm*—Schiff Hardin & Waite

(57) ABSTRACT

In a method and an apparatus for detecting the status of a battery in an implantable heart stimulator, the battery impedances measured and an increased value of the measured impedance is detected, from which an impedance based value of the remaining battery capacity is determined. The increase in impedance is analyzed to determine whether the impedance increase is a reliable indicator of the remaining battery capacity. If it is determined that the impedance increase is not reliable for determining the battery capacity, the total charge depletion of the battery is measured and a charge depletion-based value of the remaining battery capacity is determined.

10 Claims, 3 Drawing Sheets

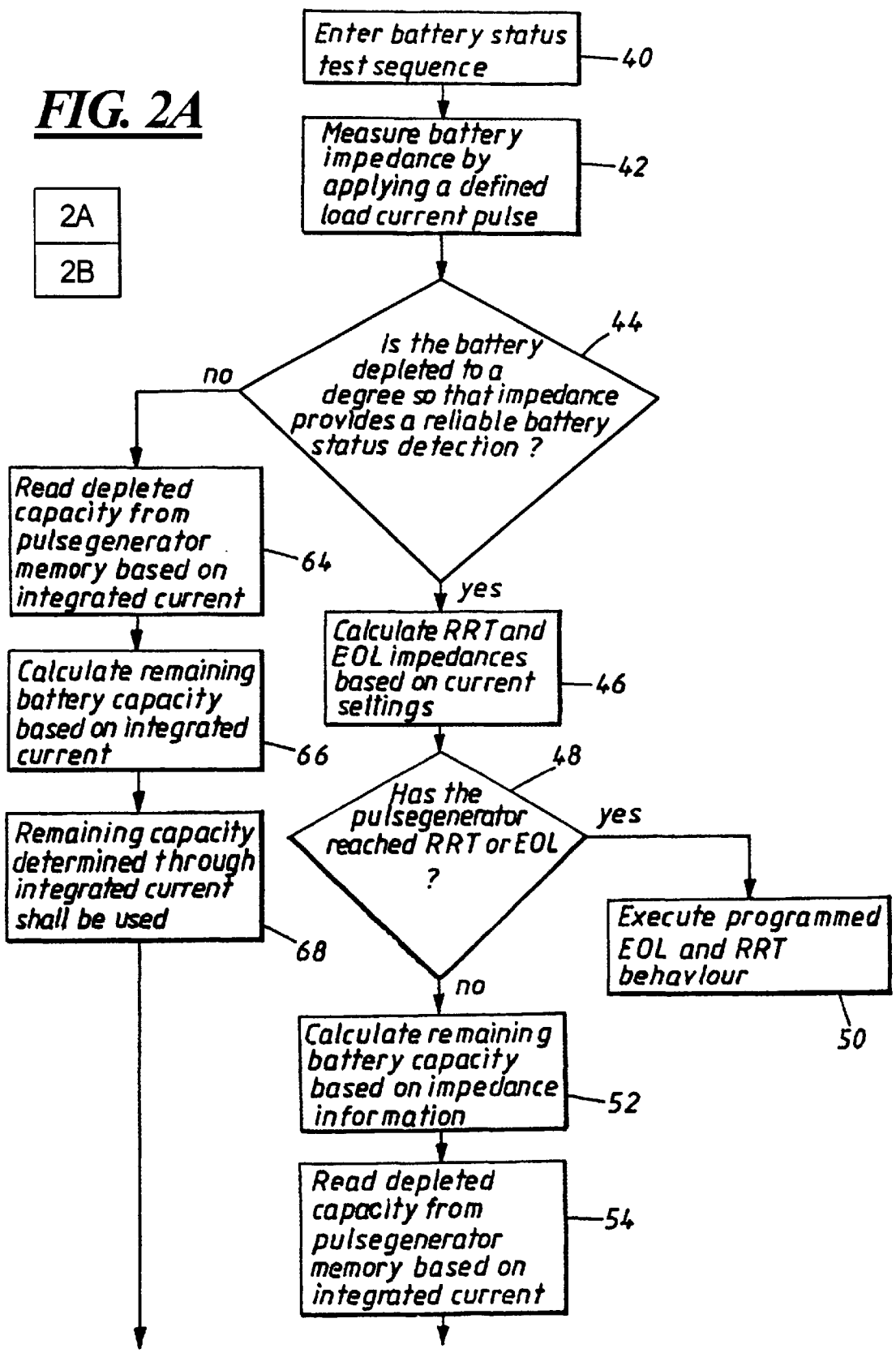

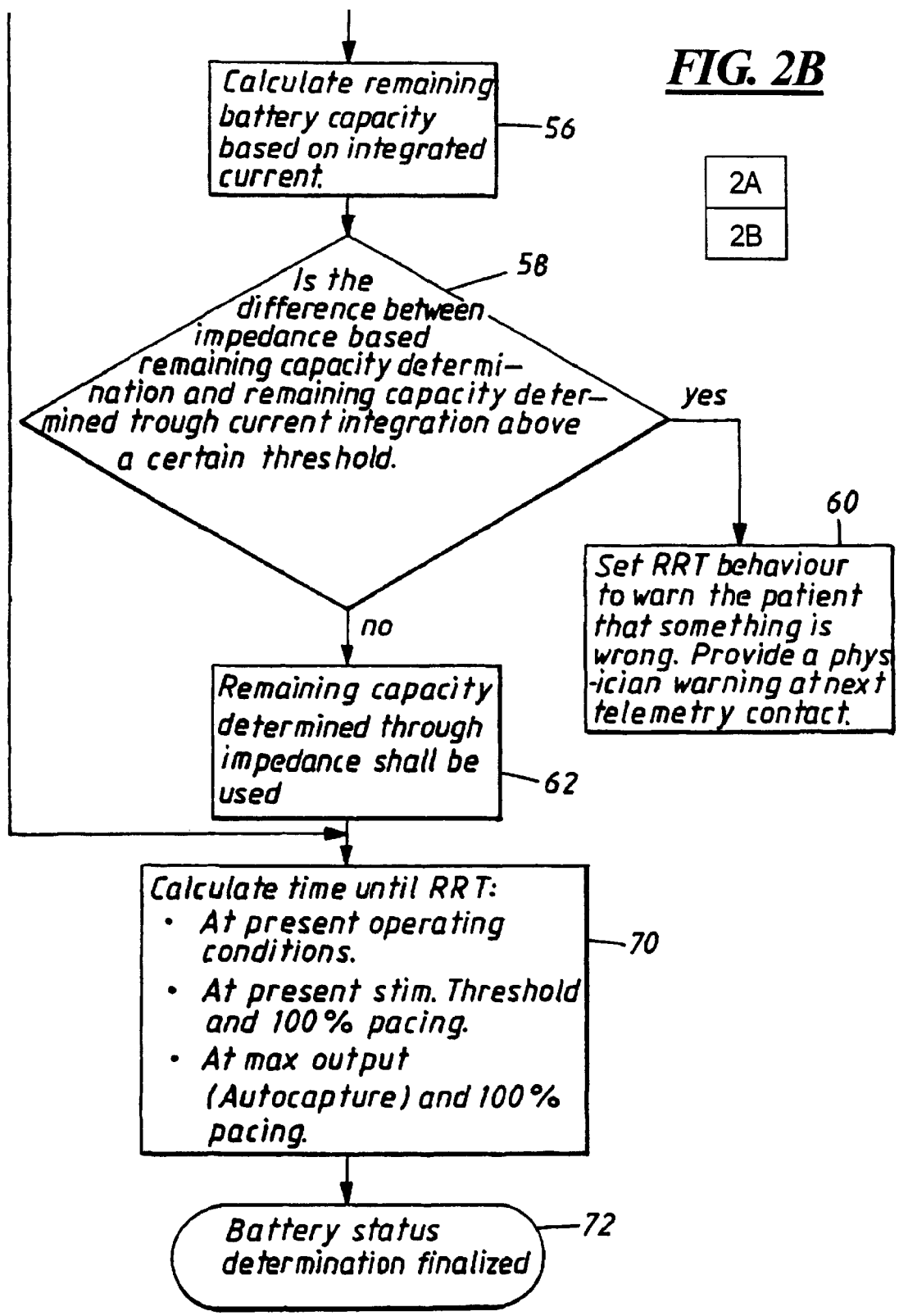

METHOD AND CIRCUIT FOR DETERMINING THE BATTERY STATUS IN A MEDICAL IMPLANT

BACKGROUND OF THE INVENTION

1. Field of the Invention

The present invention relates to a method of detecting the status of the battery of an implantable heart stimulator, and to a battery status detecting circuit for an implantable heart stimulator.

2. Description of the Prior Art

It is of utmost importance to obtain reliable information about the remaining capacity or remaining charge of batteries used in implantable devices such as heart stimulators. From this information remaining operation time of the device can be determined and this enables the physician to plan for replacement of the battery and/or the heart stimulator at the appropriate time. Several techniques have therefore been used for monitoring the battery depletion and determining the remaining battery capacity.

One of the most commonly used methods is to monitor the internal impedance of the battery. This method is also considered to be a reliable way of determining the remaining capacity of a battery. However, this technique is marred by inconveniences. Thus, for a new battery the internal impedance has a low, substantially constant value for a comparatively long time and during this time it is difficult to perform reliable measurements of the small changes which may appear in the impedance. Measurement of the internal battery impedance will consequently not provide reliable information during a comparatively long period of the early phase of battery depletion. In this phase the internal battery impedance cannot be used for determining the battery status and the remaining operation time of the heart stimulator, which is a disadvantage since it is often desirable to be able to predict already at a comparatively early stage the duration of the remaining operation time.

U.S. Pat. No. 5,370,668 discloses an implantable medical device in which internal battery impedance measurements are combined with periodic assessments of the loaded terminal voltage of the battery to obtain an elective replacement indication for when the battery depletion reaches such a level that replacement will soon be needed. The technique used in this device is adapted particularly for rejecting transients in the battery's demand as criteria for triggering an elective replacement indication.

From a theoretical point of view the ideal way of determining the remaining capacity of a battery would be measurement of the charge drawn from the battery. Such techniques are proposed in e.g. U.S. Pat. Nos. 4,715,381 and 5,769,873. In U.S. Pat. No. 4,515,381 a battery test circuit for a heart stimulator is described for identifying the consumed charge from the number of stimulation pulses emitted and from the charge related to each pulse. Other losses of current, like e.g. leakage currents, are not considered. The true remaining battery capacity could then be less than the estimated remaining capacity and consequently the remaining operation time could be overestimated. U.S. Pat. No. 5,769,873 discloses an improvement in so far that the electrical current drawn from the battery is measured and integrated. It has, however, appeared that measurement of actually depleted charge in this way will be similar to the measurements above, since spread in individual battery capacity and possible leakage currents in supply voltage stabilizing capacitors etc. are not taken into account.

SUMMARY OF THE INVENTION

An object of the present invention is to remedy the above discussed deficiencies of the prior art and to provide a battery monitoring method and circuit which allow a new way of obtaining reliable information about remaining operation time of the battery of an implantable heart stimulator all the time from the early depletion phase of the battery.

The above object is achieved in accordance with the principles of the present invention in a battery status detection circuit and method wherein battery impedance is measured and an impedance-based value of the remaining capacity of the battery is determined from a detected impedance increase, and wherein an analysis of the battery impedance increase is performed to determine whether the battery impedance is a reliable indicator of the remaining battery capacity and, if not, the total charge depleted from the battery is measured and a charge depletion-based value of the remaining capacity of the battery is determined.

Thus in the present invention measurements of the internal battery impedance, comprising the steps of measuring the impedance of the battery, detecting an increased value of the measured impedance, and determining an impedance based value of the remaining capacity of the battery from the detected impedance increase, are combined with measurements of the total charge depleted from the battery, comprising the steps of measuring the total charge depleted from the battery, and determining a charge depletion based value of the remaining capacity of the battery. The battery status detecting circuit according to the invention includes a first measurement stage for measuring the impedance of the battery, a detection unit for detecting an increased value of the measured impedance, a first determination unit for determining an impedance based value of the remaining capacity of the battery from the detected impedance increase, a second measurement unit for measuring the total charge depleted from the battery, and a second determination unit for determining a charge depletion based value of the remaining battery capacity.

Improved battery status information is obtained in this way during the entire battery discharge cycle, and a reliable estimate of the remaining operation time can be obtained at any time of the cycle. Thus, with the present invention the remaining battery capacity is determined by two separate measurements, and if the internal battery impedance measurement is assumed to give a reliable result—in the later phase of the battery discharge cycle—this measurement result will normally have priority over the measurement of depleted charge.

In an embodiment of the method according to the invention the depleted charged is measured during the whole lifetime of the battery, since this measurement can be used during the whole battery discharge cycle for estimating the remaining operating time of the battery. The impedance measurements can be started when the measured charge depleted from the battery amounts to a predetermined limit value, viz, in a later phase of the battery discharge cycle, or when other criteria relating to the remaining charge in the battery have been met, since measurements of the internal battery impedance cannot suitably be used for determining remaining operation time during the early phase of the battery discharge cycle as discussed above. Only in the later phase of this battery discharge cycle double security from two independent measurements are obtained. However, a reliable and precise estimate of the remaining operation time is, of course, most important in this later phase of the battery life time. The step of determining a charge depletion based value of the remaining battery capacity is performed only if no increased impedance is detected, suitable for a reliable impedance based determination of the remaining battery capacity, because as soon as a reliable impedance based determination of the remaining battery capacity is obtained, this result is normally considered to be more reliable and has priority over the results obtained from measurements of depleted charge. In addition to the charge-depletion value discussed above, the impedance measurement means could thus be adapted to start impedance evaluation when the measured impedance has reached a predetermined limit value, for instance a predetermined absolute value of the impedance or a predetermined slope of the impedance-charge curve. As mentioned above, the internal battery impedance is substantially constant during the early phase of the battery discharge cycle and said predetermined limit values is therefore selected to be in the vicinity of that point where the start of a significant increase in the internal impedance is expected.

In another embodiment of the method according to the invention the impedance based and the charge depletion based values of remaining battery capacity are compared and a discrepancy signal is produced if the difference between the two values of the remaining battery capacity exceeds a predetermined limit. Such a difference in a phase of the battery discharge cycle where the two measurements are supposed to give substantially the same result indicates that there is some kind of problem with the implanted stimulator.

Thus, the user can at all times obtain reliable information about remaining longevity for different operating conditions. If the remaining capacity as determined by the two methods differs significantly this indicates that there is might be an early battery depletion caused e.g. by normal spread in battery capacity or by a fault either in the electronics of the stimulator or in battery.

In an embodiment of the circuit according to the invention the charge depletion measurement means is adapted to measure the time integral of the current supplied to the stimulator electronics and the total charge contained in delivered stimulation pulses. Thus the total measured charge drawn from the battery consists of two components, i.e. the current to the stimulator electronics and the delivered stimulation pulses.

DESCRIPTION OF THE DRAWINGS

FIG. 2 is a flowchart providing an exemplary illustration of the operation of the battery status circuit according to the invention.

DESCRIPTION OF THE PREFERRED EMBODIMENTS

Figure 1:
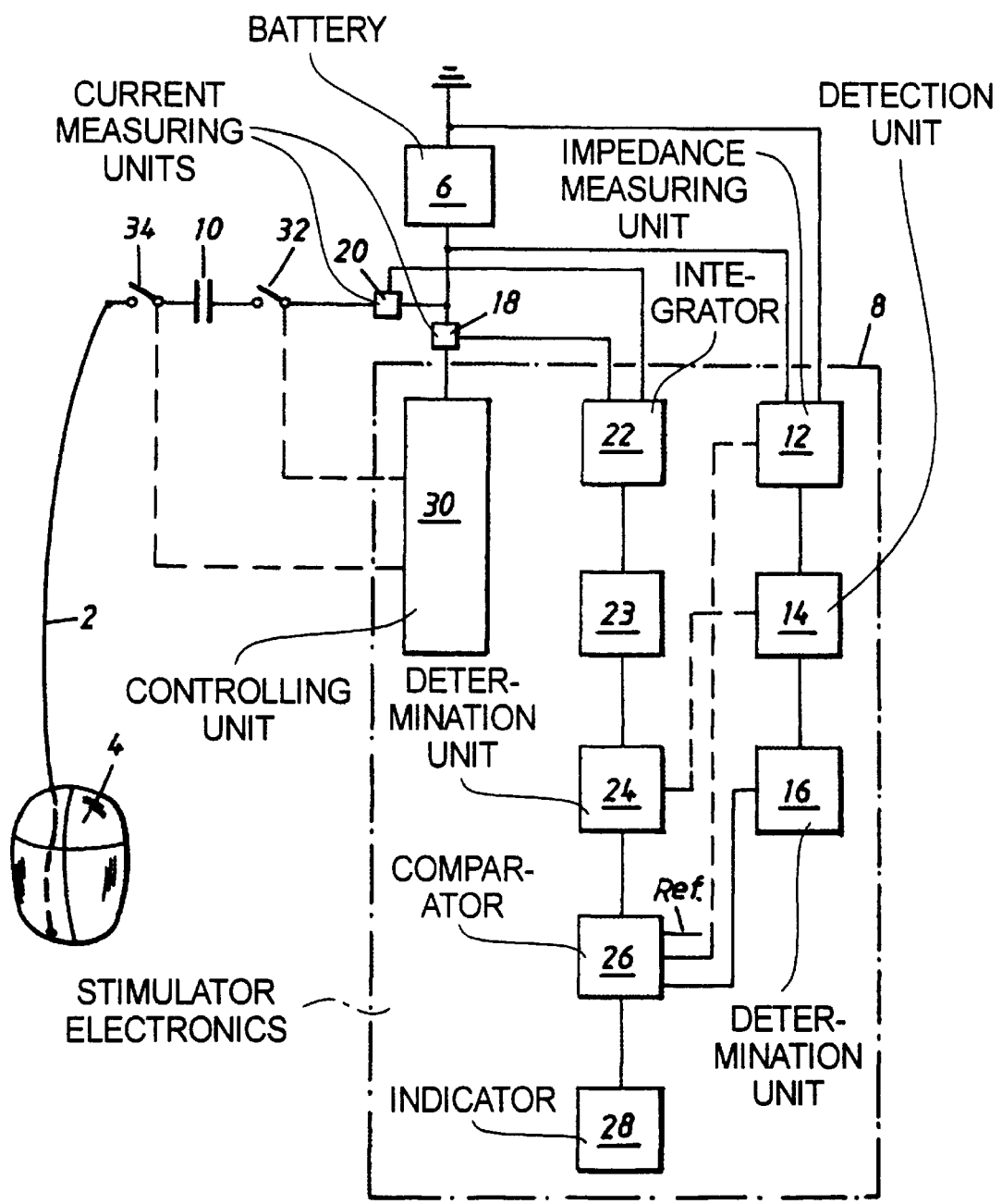
FIG. 1 is a schematic block diagram of a heart stimulator provided with an embodiment of the battery status circuit according to the invention.

FIG. 1 shows schematically in the form of a block diagram, a heart stimulator connected through a lead 2 to the heart 4 of a patient. The heart stimulator contains a battery 6 for supplying the stimulator electronics 8 with necessary electric energy and for charging a discharge capacitor 10 for delivery of stimulation pulses to the heart 4 by the lead 2.

An impedance measurement unit 12 is connected to the battery 6 for measuring the internal battery impedance. A detection unit 14 is connected to the impedance measurement unit 12 for detecting an increase of the measured internal impedance of the battery 6. A first determination unit 16 is provided for determining an impedance-based value of the remaining capacity of the battery 6 from the detected impedance increase.

Current measurement units 18, 20 are further provided 10 to continuously measure the current supplied to the stimulator electronics 8 and the current delivered to the discharge capacitor 10 for pulse delivery. An integrator 22 forms the time integral of these measured currents to determine the total charge consumed by the stimulator electronics 8 and the delivered stimulation pulses. This charge depletion measurement arrangement is adapted to measure depleted battery charge continuously during the whole lifetime of the battery. In a second determination unit 24 a charge depletion based value of the remaining battery capacity is determined from the measured total consumed charge.

A comparator 26 is provided for comparing the impedance-based value of the remaining battery capacity received from the unit 16 and the charge depletion based value received from the unit 24. If the difference between these two values of the remaining battery capacity exceeds a predetermined limit, this is noted and an indication 28 can be provided to the physician at the next follow-up.

Various controlling and timing functions of the heart stimulator are performed by the controlling unit 30. Thus, e.g. the charging of the discharge capacitor 10 and the delivery of stimulation pulses are controlled from the control unit 30 by the schematically shown switches 32 and 34 respectively.

With the above described embodiment information about the battery status is obtained during the entire battery discharge.

Several modifications of the above disclosed embodiment are, of course, possible. Thus, the impedance measurement unit 12 can be connected to said comparator 26, indicated by a dashed line in FIG. 1, for being triggered to start the impedance measurement when an increased impedance suitable for a reliable impedance-based determination of the remaining battery capacity has been detected, i.e. when certain predetermined charge-related criteria have been met. Suitable criteria are for instance that the impedance exceeds a predetermined absolute value, for instance 7500Ω or that the measured slope of the impedance-charge curve exceeds a predetermined value, for instance a slope corresponding to said predetermined absolute value.

Another criteria for the use of impedance based values is when the charge depletion based value of the remaining battery capacity has reached a predetermined limit value As mentioned above the internal battery impedance is substantially constant during the early phase of the battery discharge cycle and in this embodiment the impedance measurements are not started until such a quantity of battery charge is consumed that a significant impedance increase can be expected. Such a mode of operation can be realized with the aid of the comparator 26, in which the charge depletion based value of the remaining battery capacity is compared to a predetermined reference value Ref corresponding to a value, at which the start of a battery impedance increase can be expected.

It is also conceivable to start the impedance measurements after a predetermined time period after the implantation of the device incorporating the battery status detecting circuit.

The second determination unit 24 for determining a charge depletion based value of the remaining battery capacity can be connected to the detection unit 14, indicated by a dashed line in FIG. 1, for detecting an increased battery internal impedance such that the second determining unit 24 is triggered to determine a charge depletion based value of the remaining battery capacity only if the detection unit 14 fails to detect an increased impedance suitable for a reliable impedance based determination of the remaining battery capacity.

The function of one example of embodiment of the invention is illustrated in the flow chart of FIGS. 2A and 2B.

Thus the battery status test sequence is started, block 40, and the internal battery impedance is measured by applying a defined load current pulse to the terminals of the battery, block 42. If the battery charge is depleted to such a degree that the impedance measurements result in a reliable determination of the remaining battery capacity, recommended replacement time (RRT) for the battery or the heart stimulator and end of life (EOL) impedance are calculated based on current settings, block 46. If the heart stimulator has reached RRT or EOL, block 48, programmed RRT and EOL measures should be taken, block 50.

If RRT or EOL have not been reached, the remaining battery capacity is calculated based on the impedance obtained from the impedance measurement, block 52. Depleted battery capacity based on the integrated current and stored in a memory is read, block 54, and the remaining battery capacity is calculated based on this depleted battery capacity, block 56. The impedance based value of the remaining capacity of the battery is compared to the charge depletion based value and if the difference between these two values exceeds a certain threshold, block 58, the physician is notified at the next telemetry contact, (follow-up), block 60.

If the aforementioned difference does not exceed the threshold, block 58, the remaining battery capacity is determined from the impedance measurements, block 62. The time until RRT is then calculated for three different operating conditions, viz.

at present operating conditions (demand rate-responsive pacing corresponding to 30% pacing and the stimulation output set by beat by beat;
at 100% pacing with present stimulation threshold; and
at 100% pacing and maximum stimulation output (AutoCapture™ Pacing Systems), block 70.

If the battery is not depleted to such a degree that impedance measurements provide a reliable battery status detection, block 44, depleted battery capacity determined from integrated currents is read, block 64, and remaining battery capacity is calculated based on this read depleted battery capacity, block 66. The remaining battery capacity determined in this way is then used, block 68, for the above calculations, block 70.

The battery status determination is then finalized, block 72.

Thus, in the above described embodiment a double check of the battery status is performed by independent measurements of the internal battery impedance and the integrated currents, and in that part of the battery discharge cycle in which the impedance measurements cannot be used for determining the remaining battery capacity the remaining capacity is calculated from the total consumed charge.

The results of the battery status detection described can be displayed on the external programmer used for the heart stimulator in accordance with the following examples.

Case 1: Beginning of the Battery Depletion Phase

Battery Status

As indicated above, it is difficult to get useful battery status information during the early phase of depletion through measurements of battery characteristics like internal impedance, capacitance, unloaded voltage, chemical quantities of the battery etc. as mentioned above. The following data for the battery status thus is obtained according to the invention from the measured total depleted battery charge.

Time until recommended replacement time of the battery or the heart stimulator, RRT, with present operating conditions>60 months.

Time until RRT with 100% pacing and constant threshold (AutoCapture™ Pacing Systems)>36 months.

Time until RRT with 100% pacing and maximum stimulation output (AutoCapture™ Pacing Systems)>18 months.

Case 2: Approximately 30% of Initial Battery Capacity Remains

Battery Status

Less than 30% of initial battery capacity remains. The following information is based on battery status determination based on internal battery impedance measurements.

Time until RRT with present operating conditions>36 months.

Time until RRT with 100% pacing and constant threshold (AutoCapture™ Pacing Systems)>24 months.

Time until RRT with 100% pacing and maximum stimulation output (AutoCapture™ Pacing Systems)>12 months.

Case 3: The Heart Stimulator has Reached RRT

Battery Status

This stimulator has reached RRT.

Battery impedance=19 kΩ.

The stimulator should be replaced as soon as possible but not later than within 2 months from today. The pacing mode is changed to VVI with a pacing rate of 60 $min^{-1}$.

Case 4: The Heart Stimulator has Reached End of Life, EOL

Battery Status

This pulse generator has reached EOL.

The battery impedance=28 kΩ.

The heart stimulator should be replaced immediately. The pacing mode is changed to VVI with a pacing rate of 45 $min^{-1}$.

Thus, with the present invention reliable information about remaining battery longevity is obtained for different operating conditions. In the later phase of the battery lifetime a double check of the remaining longevity can be performed and if the results of the two independent checking methods differ significantly, this indicates an early battery depletion. Such a depletion could be caused by the normal spread in battery capacity. The spread in battery capacity implies that the battery impedance may follow several different impedance-charge curves and the above comparison of depleted charge and impedance would give information about which curve actually is relevant for the battery in question and thus better information about the remaining capacity. Another cause of early battery depletion could be a fault in the stimulator electronics or in the battery, such as an undesired leakage current. It will then be possible to notify the physician at next follow-up. It should be noted that the above method utilizing the difference from two independent checking methods only is a complement to the ordinary RRT and EOL features present in a heart stimulator, for instance of the kind described in cases 3 and 4 above.

Although modifications and changes may be suggested by those skilled in the art, it is the intention of the inventors to embody within the patent warranted hereon all changes and modifications as reasonably and properly come within the scope of their contribution to the art.

We claim:

1. A method for detecting a status of a battery in an implantable heart stimulator, comprising the steps of:

measuring an impedance of a battery in an implantable heart stimulator;

detecting an increased value of said impedance;

determining an impedance-based value of a remaining capacity of said battery from the detected increase in impedance;

analyzing said increase in impedance and determining whether said increase in impedance indicates that said impedance-based value of the remaining capacity of the battery is reliable;

if said impedance-based value of the remaining capacity of the battery is not reliable, measuring a total charge depleted from said battery; and determining a charge depletion-based value of the remaining capacity of the battery.

2. A method as claimed in claim 1 comprising comparing said impedance-based value of the remaining capacity and said charge depletion-based value of the remaining capacity and generating a discrepancy signal if a difference between said impedance-based value of the remaining capacity and said depletion-based value of the remaining capacity exceeds a predetermined limit.

3. A method as claimed in claim 1 comprising measuring the charge depleted from the battery during an entire lifetime of said battery.

4. A method as claimed in claim 1 comprising measuring said impedance of said battery when said charge depleted from said battery amounts to a predetermined limit.

5. A battery status detecting circuit for an implantable heart stimulator comprising:

a first measurement unit for measuring an impedance of a battery in an implantable heart stimulator;

a detector supplied with the measured impedance for detecting an increased value of said measured impedance;

a first determination unit for determining an impedance-based value of a remaining capacity of the battery from the detected increase in impedance;

an analyzer which analyzes said increase in impedance to determine whether said increase in impedance is reliable for indicating said remaining capacity of the battery;

a second measurement unit for measuring a total charge depleted from the battery; and a second determination unit supplied with a measurement of the depleted charge for determining a charge-depletion based value of the remaining capacity of the battery, only if said analyzer determines that said increase in impedance is not reliable for determining said remaining capacity of the battery.

6. A circuit as claimed in claim 5 comprising a comparator for comparing said impedance-based value of the remaining capacity of the battery and said charge depletion-based value of the remaining capacity of the battery, said comparator producing a comparator output if a difference between said impedance-based value of the remaining capacity of the battery and said charge depletion-based value of the remaining capacity of the battery exceeds a predetermined limit, and a signal generator, supplied with said comparator output, which generates a discrepancy signal if said comparator output is present.

7. A circuit as claimed in claim 6 further comprising an alarm supplied with said discrepancy signal which emits a humanly perceptible alarm upon activation by said discrepancy signal.

8. A circuit as claimed in claim 5 wherein said second measuring unit measures said charge depletion continuously during a whole lifetime of said battery.

9. A circuit as claimed in claim 5 further comprising stimulation electronics connected to and powered by said battery for emitting stimulation pulses, and wherein said second measurement unit measures a time integral of current supplied from said battery to said stimulator electronics and a total charge contained in said stimulation pulses, to measure said total charge depleted from said battery.

10. A circuit as claimed in claim 5 wherein said first measurement unit starts measuring said impedance when the measured battery charge depletion reaches a predetermined limit value.

* * * * *